US008326426B2

(12) United States Patent
Thornton et al.

(10) Patent No.: US 8,326,426 B2
(45) Date of Patent: Dec. 4, 2012

(54) IMPLANTABLE DEVICE WITH HEAT STORAGE

(75) Inventors: Arnold W. Thornton, Roseville, MN (US); Adrianus P. Donders, Andover, MN (US); Jason W. Sprain, Shoreview, MN (US); Koen J. Weijand, Alicante (ES)

(73) Assignee: EnteroMedics, Inc., St. Paul, MN (US)

( * ) Notice: Subject to any disclaimer, the term of this patent is extended or adjusted under 35 U.S.C. 154(b) by 677 days.

(21) Appl. No.: 12/417,791

(22) Filed: Apr. 3, 2009

(65) Prior Publication Data
US 2010/0256708 A1 Oct. 7, 2010

(51) Int. Cl.
*A61N 1/375* (2006.01)
(52) U.S. Cl. ......................................... 607/36
(58) Field of Classification Search .............. 607/36, 607/33, 61
See application file for complete search history.

(56) References Cited

U.S. PATENT DOCUMENTS

| | | |
|---|---|---|
| 3,727,616 A | 4/1973 | Lenzkes |
| 3,796,221 A | 3/1974 | Hagfors |
| 3,942,535 A | 3/1976 | Schulman |
| 4,006,748 A | 2/1977 | Schulman |
| 4,071,032 A | 1/1978 | Schulman |
| 4,082,097 A | 4/1978 | Mann et al. |
| 4,369,530 A | 1/1983 | Robinson et al. |
| 4,498,478 A | 2/1985 | Bourgeois |
| 4,577,633 A | 3/1986 | Berkovits et al. |
| 4,592,359 A | 6/1986 | Galbraith |
| 4,608,985 A | 9/1986 | Crish et al. |
| 4,612,934 A | 9/1986 | Borkan |
| 4,793,353 A | 12/1988 | Borkan |
| 4,979,511 A | 12/1990 | Terry, Jr. |
| 5,215,089 A | 6/1993 | Baker, Jr. |
| 5,251,634 A | 10/1993 | Weinberg |
| 5,263,480 A | 11/1993 | Wernicke et al. |
| 5,279,292 A | 1/1994 | Baumann et al. |
| 5,314,430 A * | 5/1994 | Bardy .............................. 607/5 |

(Continued)

FOREIGN PATENT DOCUMENTS

EP 166087 7/2006

(Continued)

OTHER PUBLICATIONS

Kilgore, K. et al., "Nerve Conduction Block Utilising High-Frequency Alternating Current," *Medical & Biological Engineering & Computing*, vol. 42, pp. 394-406 (2004).

(Continued)

*Primary Examiner* — George Manuel
*Assistant Examiner* — Joseph Stoklosa
(74) *Attorney, Agent, or Firm* — Merchant & Gould, P.C.

(57) ABSTRACT

Example embodiments of an implantable device are configured to be implanted within a patient to provide medical therapy to the patient. In general, an implantable rechargeable device includes a rechargeable battery and an electronic board assembly arranged within a case and an antenna electrically coupled to the rechargeable battery. The antenna is configured to receive power and to transfer at least a portion of the received power to the rechargeable battery for recharging. A phase change material is arranged within the case around at least a portion of the electronic board assembly. The phase change material is configured to transition from a first phase to a second phase at a transition temperature when the insulating material absorbs heat (e.g., from the electronic board assembly).

7 Claims, 5 Drawing Sheets

U.S. PATENT DOCUMENTS

| | | | |
|---|---|---|---|
| 5,344,432 A * | 9/1994 | Slettenmark et al. | 607/36 |
| 5,360,437 A | 11/1994 | Thompson | |
| 5,391,188 A | 2/1995 | Nelson et al. | |
| 5,531,778 A | 7/1996 | Maschino et al. | |
| 5,545,189 A * | 8/1996 | Fayram | 607/37 |
| 5,560,362 A | 10/1996 | Sliwa, Jr. et al. | |
| 5,658,321 A * | 8/1997 | Fayram et al. | 607/36 |
| 5,716,377 A | 2/1998 | Rise et al. | |
| 5,733,313 A | 3/1998 | Barreras, Sr. et al. | |
| 5,755,747 A | 5/1998 | Daly et al. | |
| 5,876,425 A | 3/1999 | Gord et al. | |
| 5,928,272 A | 7/1999 | Adkins et al. | |
| 6,010,803 A | 1/2000 | Heller, Jr. et al. | |
| 6,045,513 A | 4/2000 | Stone et al. | |
| 6,067,474 A | 5/2000 | Schulman et al. | |
| 6,102,874 A | 8/2000 | Stone et al. | |
| 6,167,311 A | 12/2000 | Rezai | |
| 6,205,358 B1 | 3/2001 | Haeg et al. | |
| 6,208,902 B1 | 3/2001 | Boveja | |
| 6,243,606 B1 | 6/2001 | Mann et al. | |
| 6,278,258 B1 | 8/2001 | Echarri et al. | |
| 6,280,409 B1 | 8/2001 | Stone et al. | |
| 6,285,908 B1 | 9/2001 | Mann et al. | |
| 6,356,786 B1 | 3/2002 | Rezai et al. | |
| 6,363,282 B1 | 3/2002 | Nichols et al. | |
| 6,366,814 B1 | 4/2002 | Boveja et al. | |
| 6,438,423 B1 | 8/2002 | Rezai et al. | |
| 6,471,695 B1 | 10/2002 | Behl | |
| 6,473,652 B1 | 10/2002 | Sarwal et al. | |
| 6,505,074 B2 | 1/2003 | Boveja et al. | |
| 6,505,075 B1 | 1/2003 | Weiner | |
| 6,505,077 B1 | 1/2003 | Kast et al. | |
| 6,516,227 B1 | 2/2003 | Meadows et al. | |
| 6,531,847 B1 | 3/2003 | Tsukamoto et al. | |
| 6,564,102 B1 | 5/2003 | Boveja | |
| 6,586,912 B1 | 7/2003 | Tsukamoto et al. | |
| 6,587,719 B1 | 7/2003 | Barrett et al. | |
| 6,600,956 B2 | 7/2003 | Maschino et al. | |
| 6,609,025 B2 | 8/2003 | Barrett et al. | |
| 6,611,715 B1 | 8/2003 | Boveja | |
| 6,614,406 B2 | 9/2003 | Amundson et al. | |
| 6,615,081 B1 | 9/2003 | Boveja | |
| 6,662,052 B1 | 12/2003 | Sarwal et al. | |
| 6,664,763 B2 | 12/2003 | Echarri et al. | |
| 6,690,974 B2 | 2/2004 | Archer et al. | |
| 6,755,852 B2 | 6/2004 | Lachenbruch et al. | |
| 6,760,626 B1 | 7/2004 | Boveja | |
| 6,802,839 B2 | 10/2004 | Behl | |
| 6,819,956 B2 | 11/2004 | DiLorenzo | |
| 6,850,803 B1 * | 2/2005 | Jimenez et al. | 607/61 |
| 6,879,859 B1 | 4/2005 | Boveja | |
| 6,892,097 B2 | 5/2005 | Holsheimer | |
| 6,894,456 B2 * | 5/2005 | Tsukamoto et al. | 320/107 |
| 6,895,280 B2 | 5/2005 | Meadows et al. | |
| 6,907,295 B2 | 6/2005 | Gross et al. | |
| 6,934,580 B1 | 8/2005 | Osorio et al. | |
| 7,009,362 B2 | 3/2006 | Tsukamoto et al. | |
| 7,076,307 B2 | 7/2006 | Boveja et al. | |
| 7,082,333 B1 | 7/2006 | Bauhahn et al. | |
| 7,167,750 B2 | 1/2007 | Knudson et al. | |
| 7,191,012 B2 | 3/2007 | Boveja et al. | |
| 7,318,821 B2 | 1/2008 | LaLonde et al. | |
| 7,326,433 B2 | 2/2008 | Stenzel | |
| 7,443,136 B2 * | 10/2008 | Tsukamoto et al. | 320/112 |
| 2003/0171789 A1 | 9/2003 | Malek et al. | |
| 2003/0212440 A1 | 11/2003 | Boveja | |
| 2004/0049239 A1 * | 3/2004 | Swanson et al. | 607/36 |
| 2004/0106963 A1 * | 6/2004 | Tsukamoto et al. | 607/33 |
| 2004/0249416 A1 | 12/2004 | Yun et al. | |
| 2004/0267333 A1 | 12/2004 | Kronberg | |
| 2005/0004628 A1 | 1/2005 | Goetz et al. | |
| 2005/0021092 A1 | 1/2005 | Yun et al. | |
| 2005/0038484 A1 | 2/2005 | Knudson et al. | |
| 2005/0049655 A1 | 3/2005 | Boveja et al. | |
| 2005/0065573 A1 | 3/2005 | Rezai | |
| 2005/0075693 A1 * | 4/2005 | Toy et al. | 607/60 |
| 2005/0107841 A1 | 5/2005 | Meadows et al. | |
| 2005/0131467 A1 | 6/2005 | Boveja | |
| 2005/0131484 A1 | 6/2005 | Boveja et al. | |
| 2005/0131485 A1 | 6/2005 | Knudson et al. | |
| 2005/0131486 A1 | 6/2005 | Boveja et al. | |
| 2005/0131487 A1 | 6/2005 | Boveja et al. | |
| 2005/0131493 A1 | 6/2005 | Boveja et al. | |
| 2005/0137644 A1 | 6/2005 | Boveja et al. | |
| 2005/0143787 A1 | 6/2005 | Boveja et al. | |
| 2005/0143788 A1 | 6/2005 | Yun et al. | |
| 2005/0149146 A1 | 7/2005 | Boveja et al. | |
| 2005/0192644 A1 | 9/2005 | Boveja et al. | |
| 2006/0052836 A1 | 3/2006 | Kim et al. | |
| 2006/0074450 A1 | 4/2006 | Boveja et al. | |
| 2006/0085044 A1 * | 4/2006 | Drews et al. | 607/36 |
| 2006/0195152 A1 | 8/2006 | Gerber | |
| 2006/0247711 A1 | 11/2006 | Verhoef et al. | |
| 2007/0043411 A1 | 2/2007 | Foster et al. | |
| 2007/0055330 A1 * | 3/2007 | Rutherford | 607/114 |
| 2007/0067004 A1 | 3/2007 | Boveja et al. | |
| 2007/0096686 A1 * | 5/2007 | Jimenez et al. | 320/108 |
| 2007/0250121 A1 | 10/2007 | Miesel et al. | |
| 2008/0015641 A1 | 1/2008 | Armstrong et al. | |
| 2008/0300654 A1 | 12/2008 | Lambert et al. | |
| 2008/0300656 A1 | 12/2008 | Donders et al. | |
| 2008/0300657 A1 | 12/2008 | Stultz | |
| 2008/0303480 A1 | 12/2008 | Prutchi et al. | |

FOREIGN PATENT DOCUMENTS

| | | |
|---|---|---|
| WO | WO 01/43821 | 6/2001 |
| WO | WO 03/105311 | 12/2003 |
| WO | WO 2008/151059 | 12/2008 |

OTHER PUBLICATIONS

Product Brochure, "ATROSTIM Phrenic Nerve Stimulator," AtroTech Oy, P.O. Box 28, Fin-33721,Tampere, Finland, 2 pages (Jun. 2004).

Solomonow, M. et al., "Control of Muscle Contractile Force Through Indirect High-Frequency Stimulation," *American Journal of Physical Medicine*, vol. 62, No. 2, pp. 71-82 (1983).

Fukuoka et al., "Thermal Analysis of a New High Density Package Cooling Technology Using Low Melting Point Alloys", Japanese Journal of Applied Physics, vol. 30, No. 6, Jun. 1991, pp. 1313-1319.

Horvitz et al., IASME Transactions, 2:1313 (2005).

Marongui et al., "Thermal Management of Outdoor Enclosures Using Phase Change Materials", Electronic Cooling, Jan. 1998.

Weiss, "Devices for the Treatment of Obesity: Will Understanding the Physiology of Satiety Unravel New Targets for Intervention?" J Diabetes Sci Technol, vol. 2, Issue 3, May 2008.

* cited by examiner

IMPLANTABLE DEVICE WITH HEAT STORAGE

TECHNICAL FIELD

This disclosure is directed generally to systems and methods of heat storage within an implantable electronics device, such as an implantable device having a rechargeable battery.

BACKGROUND

Over the years, numerous electrically powered medical devices have been implanted for applications such as control of the heart (cardiac pacemakers, defibrillators), neurostimulators, etc. Power to operate these devices is typically either a primary (non-rechargeable) battery, or a secondary (rechargeable) battery which receives its recharging power via an external coil which communicates inductively with an implanted coil.

From a user convenience perspective, it is desirable that the rechargeable battery be able to provide power to operate the implantable device for a significant period of time (1 day or more), so that recharging of the battery is only required infrequently. Additionally, it is desirable that when the recharging procedure is initiated, the battery is able to be fully recharged in as short a period of time as possible (ideally less than 1 hour). Charging is usually done by inductively coupling power from an external coil antenna through the skin to an implanted coil antenna. In order to achieve a short recharging time, high power must be applied to the external coil antenna. Such high power can lead to excessive heat being generated in the implanted coil, the implanted rechargeable battery, or the implanted electronics which control the recharging process, individually, or collectively.

The heat delivered into the components described above can result in a general rise in the temperature of the implanted device, and the temperature of the surface of the device presented to the adjacent tissue becomes a matter of concern, in order to avoid damage to the tissue.

Implanted devices must meet a requirement which limits the temperature rise of the surface of an implanted device to no more than 2° C. above the temperature of the surrounding tissue, as described in *The Cenelec European Standard*, EN 45502-1 (August 1997), page 18, paragraph 17.1, the disclosure of which is hereby incorporated by reference herein.

Conventional methods to regulate temperature have not proven satisfactory in meeting the conflicting requirements of the patients' convenience needs and the requirements to not damage tissue through overheating. There is, therefore, a need for an improved method and apparatus for ensuring that the surface temperature of an implanted rechargeable device does not exceed generally accepted limits.

SUMMARY

One aspect of the present disclosure relates to the control of the surface temperature of an implanted device or module. The disclosure provides an implantable rechargeable device with certain design aspects to prevent overheating of the surface of the implant during the recharging process.

Another aspect of the disclosure is to provide an implantable rechargeable device that allows inductive recharging of the energy storage module without excessive heating of any surface that can come into contact with surrounding tissue of the implanted device or associated medical devices. In some embodiments, excessive heating refers to a temperature rise exceeding 2° C. above the normal temperature of the surrounding tissue.

The invention recognizes that the principal source of heat during the recharging procedure resides not in the implanted battery or the implanted coil antenna, but rather in the associated electronics which condition and rectify the incident signal. Typically, the heat generated in the electronics can be four times the heat produced in the rechargeable battery or the implanted coil antenna. The invention also recognizes that tissue damage due to excessive heating of the surface of external components of the system or associated medical devices is prevented by including one or more insulation materials in the device or system.

In one aspect of the invention, the implanted coil antenna is located at the outer surface of the hermetically sealed device, and the frequency of the applied magnetic field is set sufficiently high (~6.78 MHz) that the penetration of the metallic components of the implant by the magnetic field is very low. In such circumstances, the source of heat within the implant does not primarily arise from eddy currents induced within the metallic elements of the implant.

Examples representative of a variety of aspects are set forth in the description that follows. The inventive aspects relate to individual features as well as combinations of features. It is to be understood that both the forgoing general description and the following detailed description merely provide examples of how the inventive aspects may be put into practice, and are not intended to limit the broad spirit and scope of the inventive aspects.

BRIEF DESCRIPTION OF THE DRAWINGS

Referring to the drawing, wherein like numerals represent like parts throughout the several views.

DETAILED DESCRIPTION

Reference will now be made in detail to exemplary aspects of the present disclosure which are illustrated in the accompanying drawings. Wherever possible, the same reference numbers will be used throughout the drawings to refer to the same or like parts.

The present disclosure relates to an implantable device and/or system configured to be implanted within a body of a patient in order to provide medical therapy to the patient. In general, the implantable device and system provides modulated electrical signals to select portions of the body of the patient (e.g., to muscles, nerves, organs, or other soft tissue). The medical therapy applied by certain embodiments of the present disclosure can be used to treat, inter alia, cardiac arrhythmias or other cardio-pulmonary conditions, neurological conditions, pancreatitis, diabetes, incontinence, gastro-esophageal reflux disease (GERD), or obesity or other gastro-intestinal disorders. The methods, devices and systems as described herein also may be applicable to pain management, tissue ablation systems, implantable drug pumps (e.g., insulin pumps), and implantable condition monitoring devices.

The following definitions are provided for terms used herein:

The "charge capacity" of a power source is the amount of charge that can be provided by the power source over a period of time. The charge current of a power source is provided in milliamperes (mA). The charge capacity is provided in milliampere-hours (mAh).

The "latent heat" of a substance is the amount of energy in the form of heat, measured in Joules per gram (J/g), released or absorbed by the substance when transitioning from a first phase to a second phase.

As the term is used herein, elements that are "operationally coupled" are arranged together with suitable intermediate components to enable the elements to perform a specified function.

A "patient" refers to any living entity (human or animal) in which the implantable device is implanted or intended to be implanted.

A "phase change material" is a substance that has a high heat of fusion, thereby allowing the material to store and/or release significant amounts of thermal energy. The phase change material changes from a first phase to a second phase when the material absorbs a sufficient amount of heat to reach a phase transition temperature. During the phase transition, the latent heat is stored while the temperature of the phase change material remains almost constant until the transition is complete. Typically, phase change materials used with embodiments of the present disclosure change from a solid to a liquid when storing thermal energy generated within the implantable device.

A "transition temperature" of a material is the temperature at which the material transitions from a first phase to a second phase. For example, a first transition temperature of water is 32° F. (0° C.) and a second transition temperature of water is 212° F. (100° C.).

Figure 1:
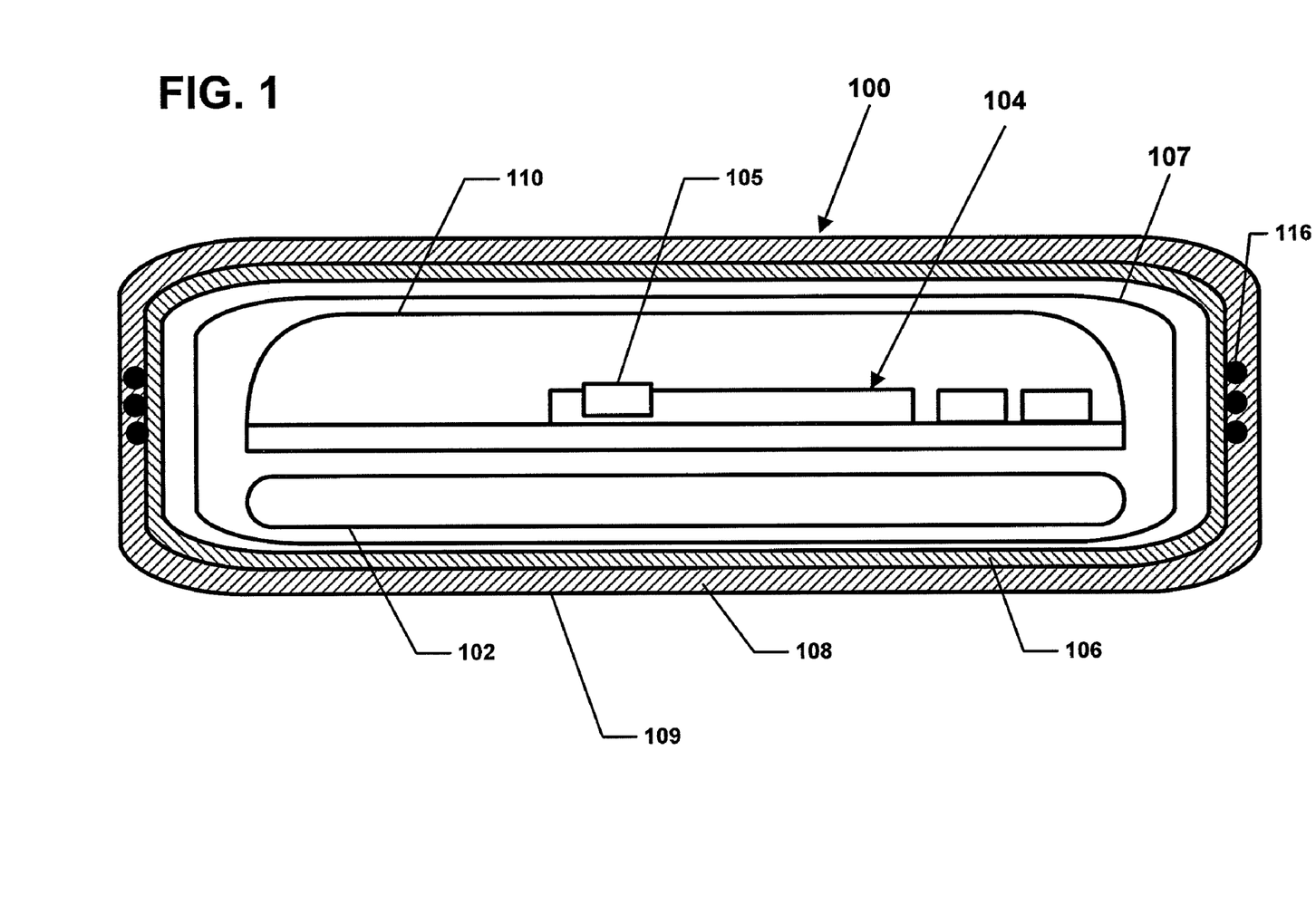
FIG. 1 is a schematic, cross-sectional view of one example implantable device including a battery and heat-absorbing material poured over or molded around an electronic board assembly in accordance with the principles of the present disclosure.

FIG. 1 is a cross-sectional view of one example implantable device 100 including a power source (e.g., a battery) 102 and an electronic board assembly 104 contained within a case 106 and operationally coupled to each other. The electronic board 104 of the implantable device 100 operates using power stored in the rechargeable power source 102. The implantable device 100 also includes an antenna 116 operationally coupled to the electronics board 104. The antenna 116 is configured to transmit and receive power and/or data (e.g., via RF signals) to and from an external device, such as an external charger, or programmer (not shown). In one embodiment, the antenna 116 includes a wire loop antenna 116. The power source 102 is recharged when a signal (e.g., an RF signal) is received at the antenna 116, induced into an electrical current, and forwarded to a charging component 105 on the electronic board 104 for storage in the power source 102. In some embodiments, the implantable device also includes a first insulative material 108 that covers all or a portion of the antenna 116 and a second insulative material, 107, that covers all or a portion of the case 106.

Some example embodiments of the implantable device 100 are configured to connect electrically to one or more lead arrangements (not shown) to provide therapy to a patient. In general, the lead arrangement includes two or more electrical lead assemblies, which are operationally coupled to areas to which therapy is to be delivered. The electronic board assembly 104 generates therapy signals and transmits the therapy signals to the lead assemblies. The lead assemblies provide therapy based on the received therapy signals.

In some embodiments, the lead assemblies can be placed on one or more nerves of a patient. For example, in one embodiment, the lead assemblies can be individually placed on an anterior vagal nerve AVN and a posterior vagal nerve PVN of a patient. In another embodiment, the lead assemblies can be placed just below the patient's diaphragm. In other embodiments, however, the lead assemblies can be secured to other suitable soft tissue to provide therapy.

The electronic board assembly 104 generates therapy signals and transmits the therapy signals to the lead assemblies. The electronic board 104 of the implantable device 100 operates using power stored in the rechargeable power source 102. The power source 102 is recharged when a signal (e.g., an RF signal) is received at the antenna 116, induced into an electrical current, and forwarded to a charging component 105 on the electronic board 104 for storage in the power source 102.

Heat is generated within the implantable device 100 during the recharging process, thereby increasing the temperature within the case 106. The electronic board assembly 104 tends to increase in temperature when the power source 102 is recharged. For example, heat can be generated when a charging component (e.g., the rectification circuit 105) of the electronic board assembly 104 activates and recharges the power source 102. Heat also can be generated when the electronic board assembly 104 generates therapy signals to provide treatment to the patient. The power source 102 also increases in temperature during charging but, typically, most of the heat is generated in the rectification circuit 105. In some embodiments, the electronic board assembly 104 (e.g., the rectification circuit 105) increases in temperature to a greater extent than the power source 102 increases in temperature. Indeed, in certain embodiments, the increase in temperature of the electronic board assembly 104 is significantly greater than the increase in temperature of the power source 102.

The heat generated within the implantable device can result in heating of the surface of the device and damage to the tissue unless the implant is designed to dissipate the heat generated. Factors in the design of the implantable device that affect heating of an external surface of the device include: a) charge rate and charge capacity of the power source; b) thermal insulation; c) phase change material; and/or 4) a sensor that senses a temperature change on the exterior of the implant and that sends a signal to terminate the charging when the temperature exceeds a preset value.

Generally, the amount of thermal energy expected to be output by the components of the implantable device is determined based on the amount of thermal energy expected to be output by the rectification circuit during the recharging process and the amount of thermal energy expected to be output by additional resistive losses (e.g., from the wiring of the electronic board 104, the current sense resistors of the electronic board 104, the power source 102, etc.) of the device 100. Of course, the implantable device can include other heat-producing components (e.g., a current protection device, a high power generator circuit, etc.) that affect the amount of thermal energy generated within the implantable device.

Recharging of the power source results in thermal energy production by the rectification circuit. For example, the amount of thermal energy put out by the electronics board can be determined based on a loss factor of the rectification circuit and the charging current. The charging current depends on the charge capacity of the power source and the charge rate. The loss factor of the rectification circuit can be determined as resistive power loss per charge current, which can be calculated based on voltage losses across the diodes of the circuit involved in the rectification process. The diodes tend to have a constant forward voltage. Accordingly, the thermal energy output by the diodes of the rectification circuit can be calculated as the charge current passed through the rectification circuit multiplied by the forward voltage, which yields total charge dissipation in terms of power (mW) per charge current (mA).

Charge Rate and Charge Capacity of the Power Source

The charge current depends on the charge capacity of the power source 102 and the rate at which the power source 102 is charged. For example, one exemplary power source 102 can have a charge capacity of 400 mAh. When charged at a charge rate of C/2 (i.e., the power store 102 is fully charged in 2 hours), the resulting charge current of 200 mA is passed through the rectification circuit over a period of 2 hours.

The selection of a suitable charge capacity and charge rate of a power source 102 is driven by daily energy needs and desired charging habits. Typically, a rapid recharge rate is advantageous. A small physical size of a power source 102 also is an advantageous property to facilitate implantation. The physical size of the power source 102 is tied to the charge capacity. In general, there is a trade off between the charge capacity and the frequency with which the power source (e.g., a battery) 102 needs to be recharged. For example, a power source 102 that has sufficient charge capacity to hold enough charge to power therapy delivery for 10 days can be recharged once every five days when the battery is 50% depleted and has 50% reserve capacity. In contrast, a power source 102 having sufficient charge capacity to power therapy delivery for only 2 days would have to be charged daily to maintain the 50% reserve capacity. In some embodiments, the size of the battery ranges from 1 to 100 mm in width, 1 to 100 mm in length, and 1 to 100 mm in depth. In some embodiments, the weight of the battery ranges from about 1 to 50 grams.

The charge current is determined based on the charge capacity of the rechargeable power source and the desired time allocated for recharging. In some embodiments, the power source is a rechargeable battery. In some embodiments, the charge capacity for a rechargeable battery can vary from about 25 to 2000 mAh, 50 to 1000 mAh, or 100 to 500 mAh. The desired time allocated for recharging depends on the effect of the charging time on battery life, patient convenience and patient compliance. In some embodiments, recharging is conducted anywhere from daily to once every 10 days. In some embodiments, the amount of time required for recharging depends on the frequency of recharging. When the recharging is conducted on a daily basis the time of recharging time is much shorter, for example, about 10 min to about 1 hour. When the recharging is conducted less frequently, the time of recharging, for example, can be from about 30 minutes to 5 hours. In some embodiments, the charge current of the battery is selected to be about 50 to 2000 mA, 100 to 1000 mA, or 200 to 500 mA. In some embodiments, the battery is selected from the group consisting of a rechargeable lithium manganese oxide battery, rechargeable lithium thionyl chloride battery, and a rechargeable lithium ion battery.

In certain embodiments, the power source 102 charges at a rate of at least C/2. One example power source 102 suitable for an implantable device 100 configured in accordance with the principles of the present disclosure has a charge capacity of about 400 mAh when charged at a rate of C/2 (i.e., the battery is charged to about 50% capacity in one hour). In such an embodiment, a charge current of about 200 mA is passed through the rectification circuit for about 2 hours. In other embodiments, the power source 102 charges more slowly than C/2.

Other resistive losses in the wiring, current sense resistors and batteries can also be estimated. In some embodiments, these resistive losses can be calculated by multiplying the square of the charging current by the sum of the resistance of the components. The resistance of a component can range from about 10 to 1000 milliohms, or 50 to 500 milliohms.

The estimation of the amount of thermal energy that is likely to be generated in the device can be calculated for a particular battery size, charge rate, and resistive losses using methods known to those of skill in the art. For example, dissipation for the rectifier is calculated as current times the forward voltage, and dissipation for resistive losses is calculated as square of the current times the sum of the resistance in the components. The amount of thermal energy released during charging can be estimated based on the thermal energy generated by the rectifier circuit during charging, and optionally, in combination with the dissipation due to components such as the battery, wiring and current sensors. The thermal energy TE output hourly from the electronic board 104 due to losses of the rectification circuit is determined by multiplying the charging current by the loss factor of the rectification circuit. In certain embodiments, a rectification circuit suitable for use with the implantable device 100 includes a loss factor ranging from about 0.3 mW/mA to about 1 mW/mA.

Insulative Material

The implantable device 100 includes a first insulative material 108 that covers all or a part of antenna 116. In embodiments, antenna 116 is wrapped around all or a portion of case 106. In embodiments, all or a portion of the antenna and/or all or a portion of the exterior of case 106 may be covered by a first insulative material. The first insulative material insulates the antenna from the effects of the dielectric constant of the surrounding tissue and may also serve to protect the tissue from damage due to any sharp edges of the antenna. In embodiments, the first insulative material is a dielectric material. In some embodiments, the first insulative material is biocompatible. Nonlimiting examples of biocompatible dielectric insulative material include biocompatible plastics such as silicone rubber, polysulphone, and TECOTHANE®.

The implantable device 100 also includes a second insulative material 107. In embodiments, the second insulative material is a thermal insulation material. Thermal insulation protects the body of the patient from an increase in temperature at an implant-tissue interface 109 resulting from operation and/or charging of the implantable device 100. The presence of the insulation and the heat sink properties of the surrounding tissue protect against a large increase in internal temperature of the device causing an increase of the surface temperature of the device of more than 2° C. In particular, the thermal insulation 107 in part protects tissue surrounding the implanted device 100 from an increase in the external surface temperature of the device 100. In one embodiment, the case 106 is at least partially covered by the thermal insulation 107.

In other embodiments, the thermal insulation 107 can be provided within the case 106 instead of, or in addition to, the outside of the case 106. In one embodiment, the case 106 is metallic. In other embodiments, however, the case 106 can be formed of any desired material.

Thermal insulation can be selected based upon the thermal resistivity of the material. Typically, a thermal insulative material insulates the exterior of the case 106 from an increase in temperature in the interior of the case of about 1 to 10° C., or more preferably about 5 to 10° C. temperature increase. For example, if the charging of the power source and the resistive losses cause an increase of the internal temperature of the interior of the case to about 43-44° C., then the insulative material maintains the exterior temperature of the case to no more than 39° C. The temperature of the exterior of the case desirably does not exceed 2° C. greater than the temperature of the surrounding tissue.

Thermal resistance of the material can be calculated by dividing the thickness of the insulative material by the surface area of the case times the thermal conductivity of the material. Depending on the thickness of the thermal insulative material and the temperature drop from the interior of the case to the exterior, a thermal insulative material can be selected that will protect the exterior from exceeding a 2° C. change from the surrounding tissue.

In some embodiments, the thermal insulation layer is about 10 micrometers to about 100 millimeters thick, about 100 micrometers to 10 millimeters, or about 200 micrometers to about 5 millimeters thick. In some embodiments, the thermal insulation material is selected from the group consisting of fiberglass, polystyrene foams, polymeric films, ceramic materials, mylar, silicon rubber, Teflon, nylon, polyethylene, silica aerogels, and yttria stabilized zirconia. In some embodiments, the insulative layer is on the outside of the case, the inside of the case or both.

In some embodiments, the first insulative material may serve also as a thermal insulation material. In that case, the first insulative material covers all or a portion of the exterior of the case. In other embodiments, a first insulative material covers all or a portion of the exterior of the case and a second insulative material covers all or a portion of the interior surface of the case. In yet other embodiments, the same insulative material covers all or a portion of the exterior of the case and/ or all or a portion of the interior of the case. The first insulative material and the second insulative material may be the same material or different materials from one another. For example, a first insulative material can be silicone rubber located on the exterior of the case and the second insulative material can be mylar located on the interior of the case.

Phase Changing Material

The implantable device 100 also includes a phase-changing, heat-absorbing material 110 at least partially surrounding components of the electronic board assembly 104. The material 110 is configured to store the heat energy generated during charging. In general, the heat-absorbing material 110 acts to inhibit temperature changes within the case 106 from raising the temperature at the implant-tissue interface 109 beyond acceptable limits.

For example, in some embodiments, the material 110 can inhibit a temperature differential at the implant-tissue interface 109 from increasing a predetermined amount beyond a predetermined baseline temperature (e.g., an average body temperature, the temperature of the tissue prior to recharging, etc.). In one embodiment, the material 110 can inhibit the temperature differential at the implant-tissue interface 109 from increasing beyond about 2° C. (about 4° F.). In other embodiments, the material 110 can inhibit temperature changes at the implant-tissue interface 109 beyond about 1° C. (about 2° F.). In other embodiments, the material 110 can inhibit temperature changes at the implant-tissue interface 109 above about 4° C. (about 7° F.).

In general, the phase change material 110 absorbs heat until the material 110 reaches a phase transition temperature (e.g., its melting temperature). The material 110 remains at an almost constant temperature while absorbing the thermal energy as the material 110 transitions between phases. For example, in one embodiment, the material 110 changes from a solid to a liquid (e.g., the material 110 melts). The material 110 continues to absorb thermal energy without a significant rise in temperature until all the material 110 is transformed (e.g., from a solid to a liquid phase). After the phase change material 110 has transitioned to the second phase, the temperature of the phase change material 110 will continue to increase at a rate inversely proportional to the mass of the phase change material 110 and inversely proportional to the specific heat in the second phase.

The phase change material 110 is generally selected to have a transition temperature in an operating temperature range reached within the case 106 during operation of the device 100 and/or recharging of the power source 102. In some embodiments, the transition temperature is greater than the temperature of the tissue surrounding the case e.g. 37° C. In some embodiments, the temperature rise within the case can be at least 1 to 10° C. or 5° C. to about 8° C. higher than any rise of the temperature of the exterior surface.

In some embodiments, the phase change material 110 is selected to have a transition temperature within a range of about 37° C. (about 100° F.) to about 80° C. (about 176° F.). In other embodiments, the phase change material 110 is selected to have a transition temperature within a range of about 37° C. (about 99° F.) to about 50° C. (about 122° F.). In certain embodiments, the phase change material 110 is selected to have a latent heat of absorption of about 40 joules/gram (J/g) to about 2260 J/g. In some embodiments, the phase change material is selected to have a latent heat of absorption of about 40 joules per gram to about 500 joules/gram, or about 100 to about 500 joules/gram. The phase change material 110 also can be selected based on other characteristics, such as small volume changes, structural integrity, and high latent heat absorption capability.

In certain embodiments, the material 110 surrounds a rectification circuit 105 of the electronic board assembly 104 that is configured to recharge the power source 102. In some embodiments, the heat-absorbing material 110 can be poured over or molded around the entire electronic board assembly 104. In other embodiments, the material 110 can surround the power source 102 instead of, or in addition to, the electronic board assembly 104.

Subsequently, the absorbed heat is released from the phase change material 110. For example, the absorbed heat can be released after the charging process has been completed. The phase change material 110 and/or the insulative layers 107 and 108 can be further selected to release the absorbed heat in a controlled manner at a rate that allows the heat to be dissipated through the tissue of the patient without raising the temperature of the implant-tissue interface 109 by more than a predetermined amount and/or above a predetermined threshold. The controlled rate of release of the heat from the phase change material 110 protects the patient from sudden and/or severe increases in temperature when components of the implantable device 100 (e.g., the electronic board assembly 104 and/or power source 102) heat up.

Factors affecting the heat dissipation rate at the implant-tissue interface 109 include the surface area of the implant-tissue interface 109 (e.g., the surface area of the implant device 100), the presence of insulation, the type of phase change material 110, and the heat sink capabilities of the surrounding tissue. Accordingly, the type of phase change material 110 and/or the insulation layers 107 and 108 provided in the implantable device 100 are selected to have a release rate that allows the surrounding tissue to dissipate the heat without a temperature differential of more than about 2° C. (about 4° F.) at the implant-tissue interface 109. In some embodiments, the phase change material 110 and/or the insulation layers 107 and 108 are selected to release the heat over a period of hours. In other embodiments, the material 110 and/or the insulation layers 107 and 108 are selected to release the heat over a period of minutes. In still other embodiments, the material 110 and/or the insulation layers 107 and 108 can be selected to release the heat over a greater or lesser period of time.

Examples of heat-absorbing phase change materials 110 suitable for use in the implantable device 100 include organic and/or inorganic materials, eutectic mixtures, and thermal composites. Suitable organic materials include paraffin wax, paraffin wax absorbed into microstructures of expanded graphite, and fatty acids. Suitable inorganic materials include salt hydrates. Nonlimiting examples of paraffin include dodecane and heneicosane. In certain embodiments, the phase change material 110 can be encapsulated within the device 100.

In general, to inhibit an increase in temperature at the implant-tissue interface 109 above a predetermined amount, the mass of the phase change material 110 is proportional to the maximum amount of heat expected to be generated within the implantable device 100 (e.g., by the electronic board assembly 104 when recharging the power source 102) and inversely proportional to the latent heat of absorption of the material. In one embodiment, the maximum amount of heat expected to be generated is the heat expected to be produced when the power source 102 is recharged to full capacity. In another embodiment, the maximum amount of heat expected to be generated is the heat expected to be produced when the power source 102 is recharged sufficiently to provide therapy until the next scheduled recharge (e.g., sufficient charge to provide therapy for one day, sufficient charge to provide therapy for one week, etc.). In some embodiments, an appropriate mass of the phase change material 100 can be determined by modeling the heat flow and temperature response of the components of the implanted device, based on the physical dimensions, specific heats, and thermal conductivities of the various sub-components, and the latent heat of the phase change material. Such predictions can be confirmed by empirical measurement and verification of the thermal behavior of the implanted component.

In some embodiments, the implantable device 100 is provided with a sufficient quantity (i.e., mass) of phase change material 110 to enable absorption of more heat than can be generated during the recharging process (e.g., when recharging from empty to full capacity). Accordingly, the total quantity of phase change material 110 does not completely transition to the second phase. In some embodiments, the implantable device 100 includes sufficient amounts of material 110 so that at least about 2% to about 50% of the phase change material 110 remains in the solid phase at the completion of the recharging process. Indeed, in some embodiments, the implantable device 100 includes sufficient amounts of phase change material 110 so that at least about 10% of the material 110 remains in the solid phase at the completion of the recharging process.

Figure 3:
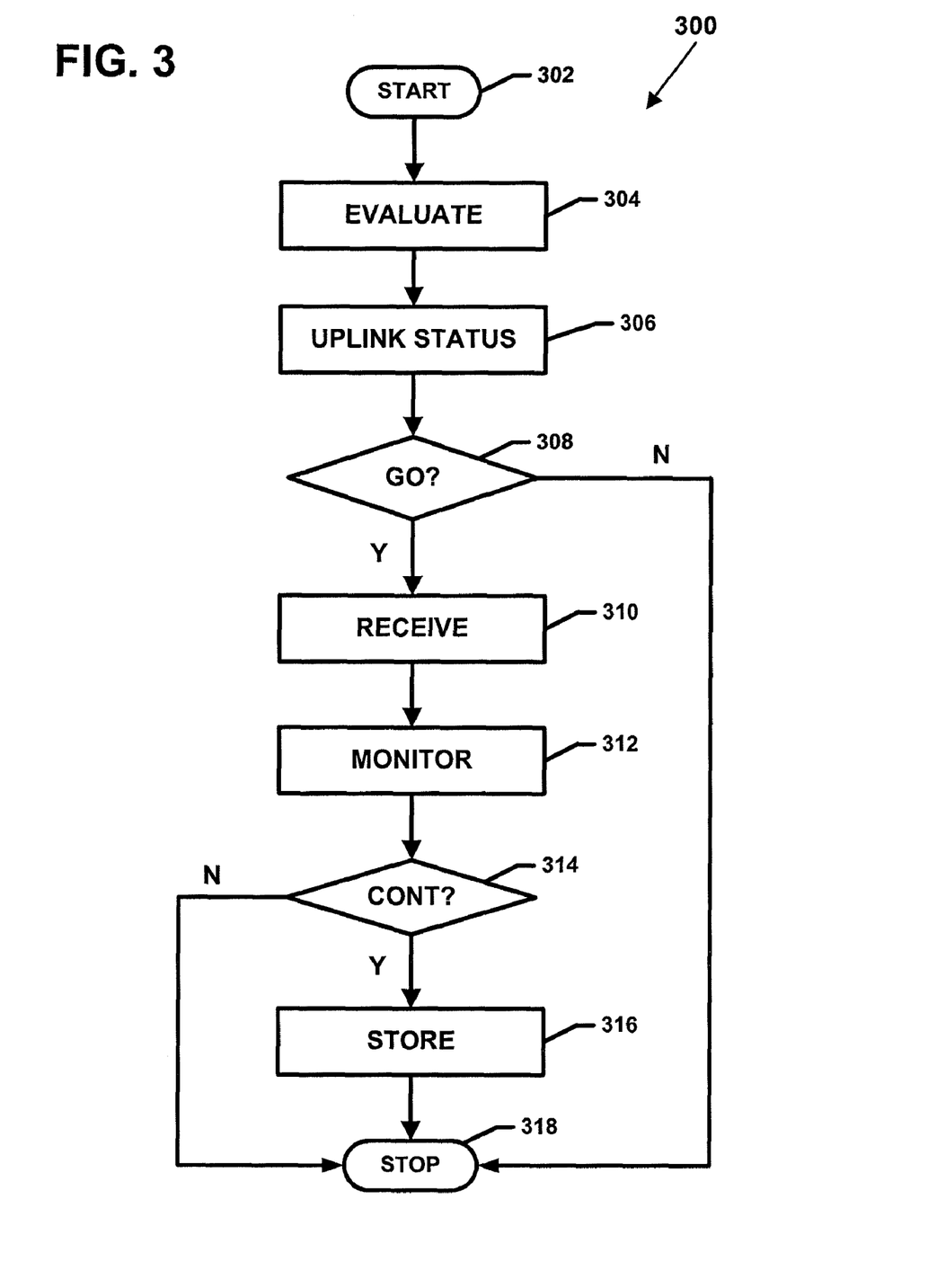
FIG. 3 is a flowchart illustrating one example charging process by which an external charger can provide power to an implantable device to recharge an implantable power source in accordance with the principles of the present disclosure.

Alternatively, in certain embodiments, the amount of phase change material 110 can be selected based on other considerations (e.g., cost, available space within the case 106, structural strength etc.). In some such embodiments, the components within the implantable device 100 can be chosen to produce no more heat than can be absorbed by the selected amount of phase change material 100. In some embodiments, the amount of phase change material can be selected to absorb at least 80% of the thermal energy. In other such embodiments, the charging schedule can be selected to produce no more heat than can be absorbed by the selected amount of phase change material 100. In still other embodiments, the implantable device 100 can be configured to terminate the charging process (e.g., charging process 300) when the heat generated by the internal components during recharging exceeds what can be absorbed by the selected amount and type of phase change material 110.

In certain embodiments, the amount of phase change material 110 sufficient for use in an implantable device 100 can be determined by dividing the amount of thermal energy expected to be output by components of the implantable device 100 (e.g., by the electronic board 104 due to losses of the rectification circuit and any additional resistive losses during recharging of the power source 102) by the latent heat of the selected type of phase change material 110. Alternatively, the type of phase change material 110 can be selected based on a pre-selected amount of phase change material 110.

Figure 2:
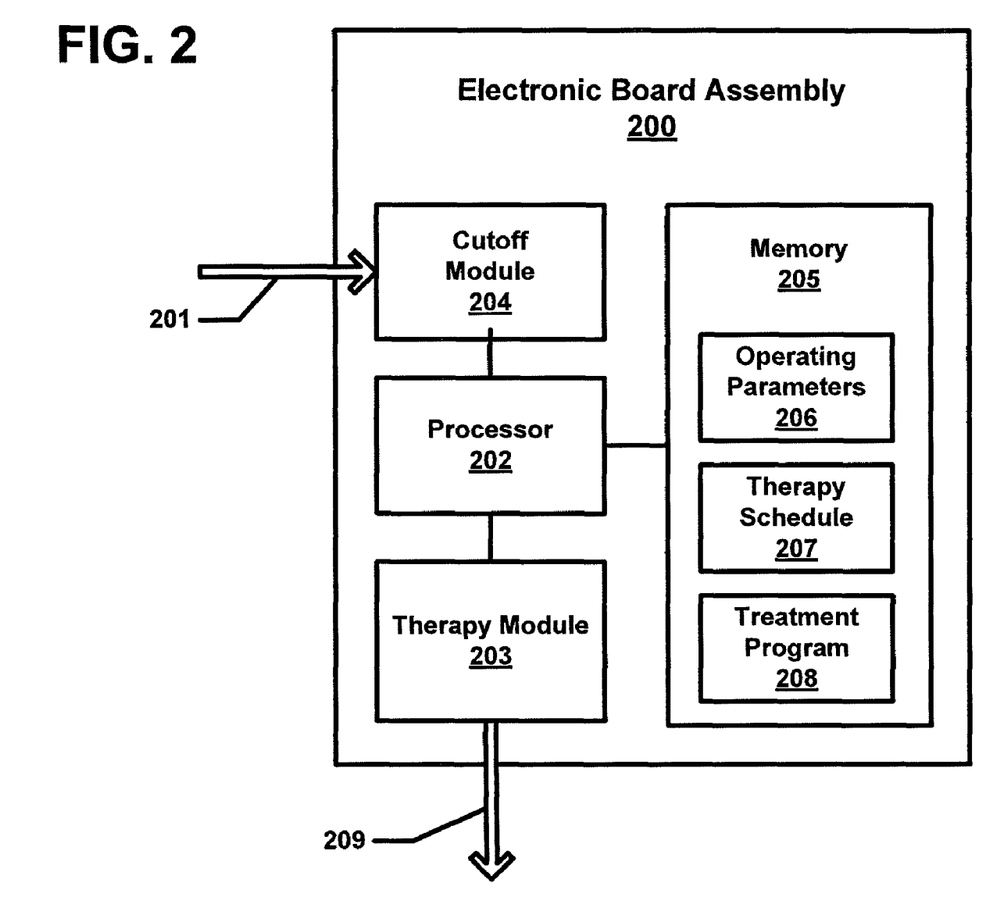
FIG. 2 is a schematic diagram of one example electronic board assembly that can be used within an implantable device configured in accordance with the principles of the present disclosure.

FIG. 2 is a schematic diagram of one example electronic board assembly 200 that can be used within an implantable device configured in accordance with the principles of the present disclosure. The electronic board assembly 200 receives incoming power and data (e.g., communication and control) signals via a link 201. The electronic board assembly 200 includes a processor 202, a therapy module 203, and a memory 205. Operating parameters 206 of the implantable device, therapy schedules 207, and treatment programs 208 can be stored within the memory 205. The baseline temperature also can be stored in memory 205.

In operation, the therapy module 203 generates a therapy signal based on the treatment programs 208 and therapy schedule 207 stored in the memory 205. The therapy signal can be output from the electronic board assembly 200 along output line 209. For example, the therapy signal can be transmitted from therapy module 203 to one or more lead arrangements to operate the lead assemblies. In some embodiments, the lead assemblies up-regulate and/or down-regulate nerves of a patient based on the therapy signals provided by the therapy module 203. In one embodiment, the lead assemblies include distal electrodes, which are placed on one or more nerves of a patient. In other embodiments, however, the electrodes can be placed on or near other types of soft tissue (e.g., muscles).

In one example embodiment, an example rectification circuit of the electronic board 104 is selected to have a loss factor of about 0.5 mW/mA, the power source 102 is selected to have a charge capacity of about 400 mAh, and the charge rate is selected to be C/2. The thermal energy TE(RC) output hourly from the electronic board 104 based on the rectification circuit in this example embodiment is shown in the following equation (1):

$$TE(RC) = 200 \text{ mA} * 0.5 \text{ mW/mA} = 100 \text{ mW} = 0.1 \text{ J/sec} \quad (1)$$

Accordingly, the amount of thermal energy TE(RC) output from the electronic board 104 based on the rectification circuit each day during the recharging period is determined according to the following equation (2):

$$TE(RC) = 0.1 \text{ J/sec} * 60 \text{ sec/min} * 60 \text{ min/hr} * 2 \text{ hrs} = 720 \text{ J} \quad (2)$$

In general, the thermal energy TE(AR) output by the electronic board 104 based on additional resistive losses is determined by multiplying the square of charge current by the additional resistive losses. Some non-limiting examples of additional resistive losses of the electronic board 104 include losses based on the resistance of a current sense resistor of the board 104, the resistance of the power source 102, and the resistance of the wiring of the board 104.

In one example embodiment, the current sense resistor of the board 104 is selected to have a resistance of about 100 milliohm, the power source 102 is selected to have a resistance of about 400 milliohm, and the wiring of the board 104 is selected to have a resistance of about 50 milliohm. The thermal energy TE(AR) output hourly from the electronic board 104 based on the additional resistive losses in this example embodiment is shown in the following equation (3):

$$TE(AR)=0.04\ A^2*0.550\ ohm=22\ mW=0.022\ J/sec \quad (3)$$

Accordingly, the amount of thermal energy TE(AR) output from the electronic board 104 based on the additional resistive losses each day during the recharging period is determined according to the following equation (4):

$$TE(AR)=0.022\ J/sec*60\ sec/min*60\ min/hr*2\ hrs=158\ J \quad (4)$$

Accordingly, the amount A of heat-absorbing material 110 sufficient to absorb the thermal energy output from the electronic board 104 (at a constant temperature during the phase change transition) during the recharging process is determined according to the following equation (5):

$$A=[TE(RC)+TE(AR)]/(\text{the latent heat of the material}) \quad (5)$$

In certain embodiments, the material 110 is selected to have a latent heat of fusion ranging from about 40 J/g to about 2260 J/g. Indeed, in certain embodiments, the material 110 is selected to have a latent heat of fusion ranging from about 150 J/g to about 300 J/g. One non-limiting example of a heat-absorbing material 110 having such a latent heat of fusion is dodecane. Other materials of the paraffin series also can have suitable latent heat of fusion. In one embodiment, the material 110 is formed from absorbing a paraffin material into a microstructure of expanded graphite. In other embodiments, the material 110 can be selected to have a higher or lower latent heat of fusion as appropriate.

In one example embodiment, the material 110 is selected to have a latent heat of about 200 J/g. Accordingly, the amount A of heat-absorbing material 110 sufficient to absorb the thermal energy output from the electronic board 104 is determined by the following equation (6):

$$A=[720\ J+158\ J]/200\ J/g=878\ J/200\ J/g=4.4\ g \quad (6)$$

Termination of Charging based on External Temperature Change

In embodiments, the device includes sensors or monitors of the external temperature of the device and modules that terminate charging if the external temperature exceeds more than 2° C. Referring to FIG. 3, a monitor operation 312 measures any rise in temperature at the tissue-implant interface (e.g., the temperature of the external surface of the device) during the transmission of power from the external charger to the implantable device. A second determination module 314 stops the charging process 300 if the rise in temperature exceeds a predetermined threshold. For example, in one embodiment, the second determination module 314 may stop the charging process 300 if the rise in temperature of the implantable device exceeds about 2° C. (about 4° F.). The second determination module 314 also can stop the charging process 300 if the temperature of the implant-tissue interface meets or exceeds a predetermined temperature.

A store operation 316 stores the obtained power in the implantable power source (e.g., power source 102). The charging process 300 completes and ends at a stop module 318. In the above embodiment, the implantable device controls when and how much power is obtained from the external charger. In another embodiment, the external charger controls when and how much power to send to the implantable device. For example, the external charger can determine a sufficient amount of power to send based on the uplinked operational status information. The steps of charging process 300 need not be performed in the exact order shown in FIG. 3. Also, certain steps may be repeated throughout the charging process 300. For example, the uplink and monitor operations 306, 312 can be repeated at periodic intervals during the charging process. In one embodiment, one or both of these operations 306, 312 are repeated about five times per second.

Figure 4:
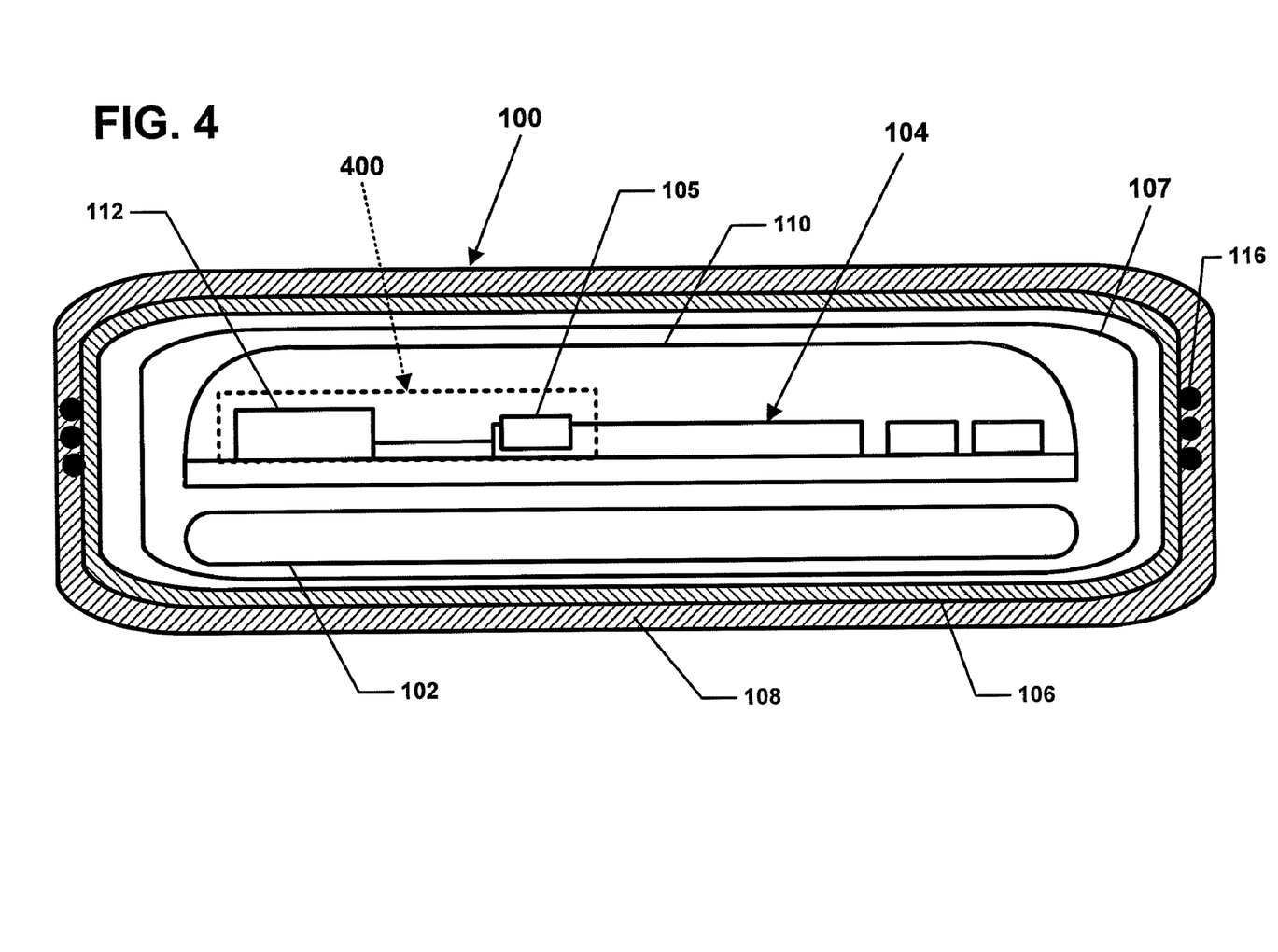
FIG. 4 is a schematic, cross-sectional view of another example implantable device including a battery and heat-absorbing material poured or molded over or around an electronic board assembly and a temperature sensor in accordance with the principles of the present disclosure.

Referring to FIG. 4, in some embodiments, the implantable device 100 also includes a cutoff assembly 400 to aid in limiting the increase in temperature at the implant-tissue interface 109. During the course of operation and recharging of the device 100, the temperature within the case 106 may increase beyond the ability of the phase change material 110 and/or thermal insulation 107 and 108 to absorb and manage. Such circumstances may occur when a patient or physician exceeds a recommended time period for the recharging procedure. Such circumstances also may occur during a component failure leading to an increase in the recharging rate. In such circumstances, the cutoff assembly 400 terminates one or more heat-generating operations of the implantable device 100 to allow dissipation of the heat prior to generating additional heat.

The cutoff assembly 400 determines when to terminate the recharging process based on the temperature of an estimated temperature of the implant-tissue interface 109 and the rate of temperature change. For example, the cutoff assembly 400 can terminate a recharging process of the implantable device 100 before the temperature of the implant-tissue interface 109 rises above about 2° C. (about 4° F.). The temperature of the interface 109 can be estimated based on the temperature within the case 106, the properties of the thermal insulation 107 or 108, and the properties of the phase change material 110.

In one embodiment, the cutoff assembly 400 includes a temperature sensor 112 (FIG. 4) configured to measure the temperature within the case 106. In another embodiment, the temperature sensor 112 is configured to measure the temperature of the phase change material 110. The temperature sensor 112 can be coupled to a cutoff module on the electronic board assembly 104 (e.g., cutoff module 204 on board 200 in FIG. 2). The cutoff module can trigger cessation of the recharging process if the measured temperature exceeds a predetermined threshold. For example, in one embodiment, the temperature sensor 112 can trigger cessation of the recharging process if the temperature of the phase change material 110 exceeds the transition temperature of the phase-changing material 110 by a predetermined margin. In another embodiment, the temperature sensor 112 can trigger cessation of the recharging process if the temperature within the case 106 exceeds a threshold temperature (e.g., a threshold temperature stored in the memory 203 of the board 200 of FIG. 2). In some embodiments, the threshold temperature is at least 39° C. or greater.

FIG. 3 is a flowchart illustrating one example charging process 300 by which the external charger can provide power to an implantable device (e.g., implantable device 100 of FIG.

1) to recharge an implantable power source (e.g., power source 102 of FIG. 1). The charging process 300 begins at a start module 302, performs any appropriate initialization processes, and proceeds to an evaluate operation 304. In general, the evaluate operation 304 determines an operating status of the implantable device.

In one embodiment, the evaluate operation 304 determines the level of charge stored in the implantable power source. For example, the evaluate operation 304 can determine a battery voltage. In another embodiment, the evaluate operation 304 determines whether it is preferable to recharge the battery voltage with a high level of power or a low level of power. In another embodiment, the evaluate operation 304 determines the temperature of the implant-tissue interface (e.g., interface 109 of FIG. 1) prior to receiving any power transmissions.

An uplink operation 306 transmits the operational status information of the implantable device to an external charger. For example, the operational status information can include a power level of the implantable power source. The operational status information also can include an indication of whether power is desired from the external charger to recharge the implantable power source. In certain embodiments, the operational status information includes an indication of whether the external charger should send a high level power transmission (e.g., large amplitude signal) or a low level power transmission (e.g., small amplitude signal). For example, the implantable device can determine an appropriate level of power based on the level of charge stored in the implantable power source as determined in the evaluate operation 304.

If a first determination module 308 determines the implantable power source should not be charged, then the charging process 300 completes and ends at a stop module 318. In one embodiment, the first determination module 308 can determine the implantable power source should not be charged when the implantable power source has at least a threshold level of charge. In another embodiment, the first determination module 308 can determine the implantable power source should not be charged when the implantable power source exceeds a threshold level of charge. In another embodiment, the first determination module 308 can determine the implantable power source should not be charged when a temperature of the implant-tissue interface meets or exceeds a threshold level.

If the first determination module 308 determines the implantable power source should be charged, however, then a receive operation 310 obtains power from the external charger in response to the uplinked operational status information. In one embodiment, the obtained power transmission does not include any data signals (e.g., information and/or commands). For example, in one embodiment, the receive operation 310 may obtain only an unmodulated signal. In one embodiment, the implantable device obtains a power transmission having a high amplitude (e.g., about 100-200 mA). In another embodiment, the implantable device obtains a power transmission having a low amplitude (e.g., about 50 mA). In one embodiment, the receive operation 310 may receive a power transmission over a period of about one minute. In other embodiments, the power transmission can have any desired duration (e.g., milliseconds, seconds, minutes, hours, etc.).

A monitor operation 312 measures any rise in temperature at the tissue-implant interface (e.g., the temperature of the external surface of the device) during the transmission of power from the external charger to the implantable device. A second determination module 314 stops the charging process 300 if the rise in temperature exceeds a predetermined threshold. For example, in one embodiment, the second determination module 314 may stop the charging process 300 if the rise in temperature of the implantable device exceeds about 2° C. (about 4° F.). The second determination module 314 also can stop the charging process 300 if the temperature of the implant-tissue interface meets or exceeds a predetermined temperature.

A store operation 316 stores the obtained power in the implantable power source (e.g., power source 102). The charging process 300 completes and ends at a stop module 318. In the above embodiment, the implantable device controls when and how much power is obtained from the external charger. In another embodiment, the external charger controls when and how much power to send to the implantable device. For example, the external charger can determine a sufficient amount of power to send based on the uplinked operational status information. The steps of charging process 300 need not be performed in the exact order shown in FIG. 3. Also, certain steps may be repeated throughout the charging process 300. For example, the uplink and monitor operations 306, 312 can be repeatedly at periodic intervals during the charging process. In one embodiment, one or both of these operations 306, 312 are repeated about five times per second.

Referring to FIG. 4, in some embodiments, the implantable device 100 also includes a cutoff assembly 400 to aid in limiting the increase in temperature at the implant-tissue interface 109. During the course of operation and recharging of the device 100, the temperature within the case 106 may increase beyond the ability of the phase change material 110 and thermal insulation 107 to absorb and manage. Such circumstances may occur when a patient or physician exceeds a recommended time period for the recharging procedure. Such circumstances also may occur during a component failure leading to an increase in the recharging rate. In such circumstances, the cutoff assembly 400 terminates one or more heat-generating operations of the implantable device 100 to allow dissipation of the heat prior to generating additional heat.

The cutoff assembly 400 determines when to terminate the recharging process based on the temperature of an estimated temperature of the implant-tissue interface 109 and the rate of temperature change. For example, the cutoff assembly 400 can terminate a recharging process of the implantable device 100 before the temperature of the implant-tissue interface 109 rises above about 2° C. (about 4° F.). The temperature of the interface 109 can be estimated based on the temperature within the case 106, the properties of the thermal insulation 107 and 108, and the properties of the phase change material 110.

In one embodiment, the cutoff assembly 400 includes a temperature sensor 112 (FIG. 4) configured to measure the temperature within the case 106. In another embodiment, the temperature sensor 112 is configured to measure the temperature of the phase change material 110. The temperature sensor 112 can be coupled to a cutoff module on the electronic board assembly 104 (e.g., cutoff module 204 on board 200). The cutoff module can trigger cessation of the recharging process if the measured temperature exceeds a predetermined threshold. For example, in one embodiment, the temperature sensor 112 can trigger cessation of the recharging process if the temperature of the phase change material 110 exceeds the transition temperature of the phase-changing material 110 by a predetermined margin. In another embodiment, the temperature sensor 112 can trigger cessation of the recharging process if the temperature within the case 106 exceeds a threshold temperature (e.g., a threshold temperature stored in the memory 203 of the board 200 of FIG. 2).

Sometimes, phase transitions from a lower energy state to a higher energy state (e.g., from a solid phase to a liquid phase, or from a liquid phase to a gas phase) are accompanied by a change in volume of the phase-changing, heat-absorbing material 110. For example, the phase change material 110 can expand from a first volume (see 110 of FIG. 5) to a second volume (see 110' of FIG. 5). Accordingly, embodiments of the implantable device 100 include a case 106 sized to provide sufficient room for the phase change material 110 to expand. For example, the case 106 can be sufficiently sized to leave a gap 114 (FIG. 5) between the electronic board assembly 104 and the case 106. In some cases, the phase change material 110 can decrease in volume as the phase changes. In such cases, the design of the implantable device 100 must be such that it can accommodate such volume changes.

Figure 5:
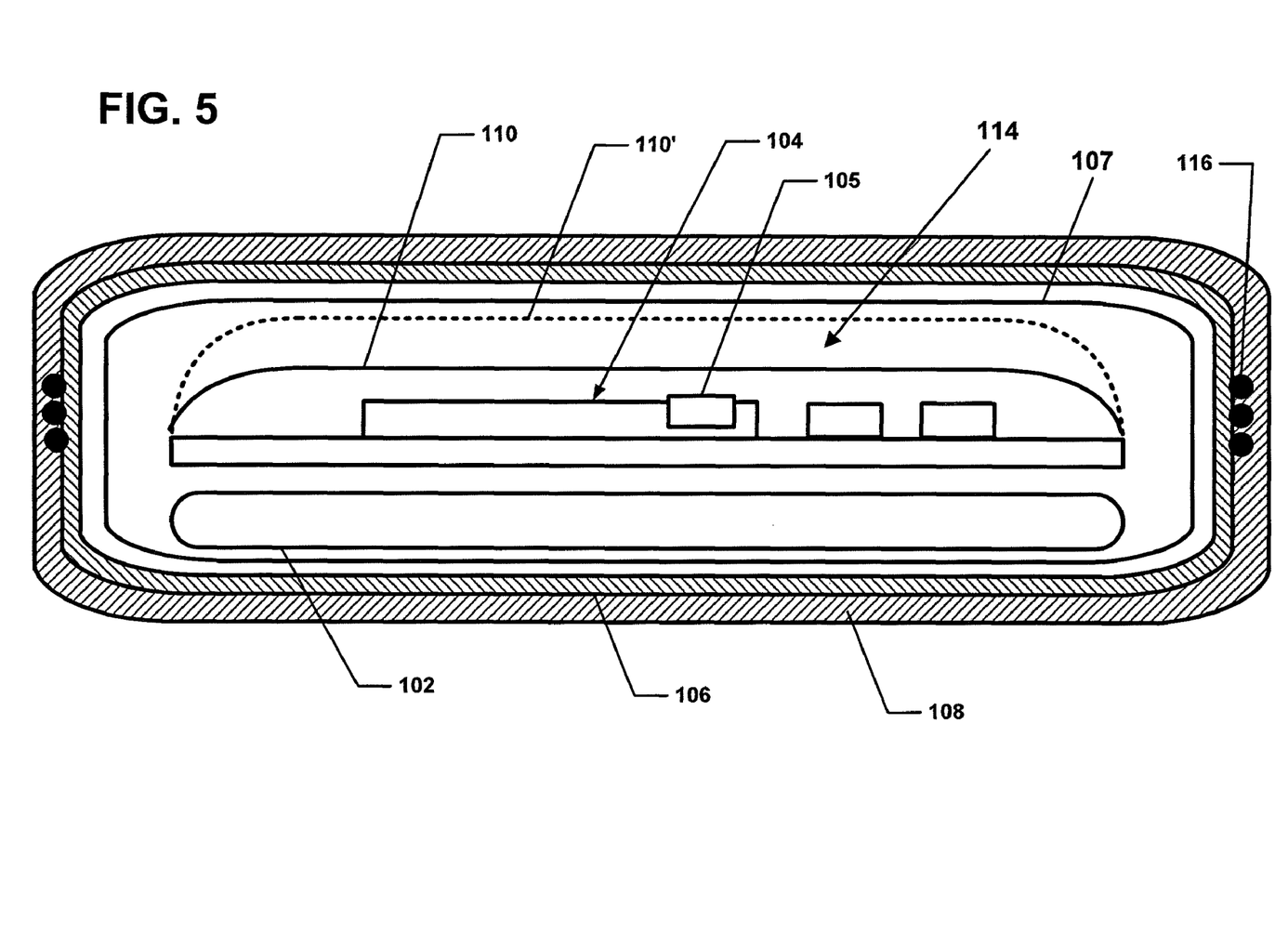
FIG. 5 is a schematic, cross-sectional view of the example implantable device of FIG. 1 illustrating a transition between a lower energy state of the heat-absorbing material to a higher energy state in accordance with the principles of the present disclosure.

In one embodiment, the gap 114 contains a partial or total vacuum 114 into which the phase change material 110 can expand. In other embodiments, the gap 114 contains an inert gas or other gas that is configured to compress to allow for expansion of the phase change material 110. In some embodiments, the case is filled with hydrochlorofluorcarbon (HCFC), chlorinated fluorocarbon, or perfluorocarbons. In one embodiment, the gas within the gap 114 is contained at normal atmospheric pressure. In another embodiment, the gas within the gap 114 is contained at a reduced pressure. In certain embodiments, the phase change material 110 is contained (i.e., encapsulated) within a housing (not shown). In such embodiments, the housing is sized and configured to accommodate expansion and shrinkage of the phase change material 110 during operation and recharging of the device 100.

The disclosure also provides a method of manufacturing a rechargeable, implantable device comprising: arranging a rechargeable battery and an electronic board assembly within a case, wherein the case comprises a thermal insulating material covering all of a portion of the case, and wherein the rechargeable battery and the electronic board assembly are electrically coupled to each other; electrically coupling an antenna to the rechargeable battery and the electronic board assembly; and operationally coupling a phase change material at or adjacent the electronic board assembly. In some embodiments, operationally coupling the phase change material includes pouring the phase change material over at least a portion of the electronic board assembly. In other embodiments, operationally coupling the phase change material includes molding the phase change material around at least a portion of the electronic board assembly. In yet other embodiments, operationally coupling the phase change material includes pouring the phase change material over at an entirety of the electronic board assembly or over at an entirety of the electronic board assembly and the power source.

In some embodiments, the method further comprises reducing the pressure of the case subsequent to arranging the phase change material within the case. In other embodiments, the method further comprises backfilling the case with an inert gas or organic material subsequent to arranging the phase change material within the case. In embodiments, the organic material is selected from the group consisting of perfluorocarbon, hydrochlorofluorocarbon (HCFC), and hydrochlorofluorocarbon (HCFC).

The disclosure provides a method of designing an implantable device in order to minimize the risk of increasing the temperature of the exterior of the device more that 2° C. than a predetermined value such as the temperature of the surrounding tissue (e.g. about 35 to 40° C.). The method comprises: a) selecting a rechargeable power source having a certain charge capacity; b) estimating the maximum thermal energy produced in the device that is generated during recharging of the rechargeable power source; c) selecting the amount and type of phase change material that can absorb at least 80% of the thermal energy generated; and selecting the amount and type of thermal insulating material to inhibit a temperature increase of more than 2° C. on the exterior of the device.

The above specification provides examples of how certain inventive aspects may be put into practice. It will be appreciated that the inventive aspects can be practiced in other ways than those specifically shown and described herein without departing from the spirit and scope of the inventive aspects. Any publications referred to herein are hereby incorporated by reference.

We claim:

1. A method of manufacturing an implantable device comprising:
   arranging a rechargeable battery and an electronic board assembly within a case, wherein the case comprises a thermal insulating material and wherein the rechargeable battery and the electronic board assembly are electrically coupled to each other, and wherein the electronic board assembly is active when generating therapy signals and when the rechargeable battery is being recharged;
   electrically coupling an antenna to the rechargeable battery and the electronic board assembly; and
   arranging a phase change material within the case in an amount sufficient to inhibit a rise in temperature at the implant-tissue interface by more than about 2° C. when the electronic board assembly is active, wherein arranging the phase change material includes pouring the phase change material over at least a portion of the electronic board assembly.

2. The method of claim 1, wherein arranging the phase change material includes pouring the phase change material over an entirety of the electronic board assembly.

3. The method of claim 1, wherein arranging the phase change material includes pouring the phase change material over at an entirety of the electronic board assembly and the power source.

4. The method of claim 1, further comprising reducing the pressure of the case subsequent to arranging the phase change material within the case.

5. The method of claim 1, further comprising backfilling the case with an inert gas subsequent to arranging the phase change material within the case.

6. The method of claim 5, further comprising backfilling the case with an organic material.

7. The method of claim 6, wherein the organic material is selected from the group consisting of perfluorocarbon, hydrochlorofluorocarbon (HCFC), and hydrochlorofluorocarbon (HCFC).

* * * * *